United States Patent
Cho et al.

(10) Patent No.: US 11,517,216 B2
(45) Date of Patent: Dec. 6, 2022

(54) BODY COMPOSITION ANALYSIS SYSTEM

(71) Applicant: ELECTRONICS AND TELECOMMUNICATIONS RESEARCH INSTITUTE, Daejeon (KR)

(72) Inventors: Min-Hyung Cho, Daejeon (KR); Young-deuk Jeon, Sejong (KR); Bon Tae Koo, Daejeon (KR); Mun Yang Park, Daejeon (KR); Youngseok Baek, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 505 days.

(21) Appl. No.: 16/248,582

(22) Filed: Jan. 15, 2019

(65) Prior Publication Data
US 2019/0239771 A1    Aug. 8, 2019

(30) Foreign Application Priority Data
Feb. 6, 2018 (KR) .................. 10-2018-0014770

(51) Int. Cl.
*A61B 5/0537* (2021.01)
*G01N 27/02* (2006.01)
(Continued)

(52) U.S. Cl.
CPC .......... *A61B 5/0537* (2013.01); *A61B 5/4869* (2013.01); *A61B 5/7278* (2013.01);
(Continued)

(58) Field of Classification Search
CPC ... A61B 5/0537; A61B 5/4869; A61B 5/7225; A61B 5/7278; G01N 27/028; G01N 33/4833
See application file for complete search history.

(56) References Cited

U.S. PATENT DOCUMENTS

| 5,063,937 A | 11/1991 | Ezenwa et al. |
| 7,706,872 B2 | 4/2010 | Min et al. |
| (Continued) | | |

FOREIGN PATENT DOCUMENTS

| KR | 101114671 B1 | 3/2012 | |
| KR | 101190811 B1 | 10/2012 | |
| WO | WO-2017007574 A1 * | 1/2017 | ........... A61B 5/7225 |

OTHER PUBLICATIONS

Long, Steve, Presentation on Fundamentals of Mixer Design, Apr. 17, 2001, Agilent Technologies (Year: 2001).*

(Continued)

*Primary Examiner* — Christian Jang
*Assistant Examiner* — Anna Roberts

(57) ABSTRACT

The inventive concept relates to a body composition analysis system. A body composition analysis system according to an embodiment of the inventive concept includes a sinusoidal signal generator, a synchronous detector, and a bioimpedance analyzer. The sinusoidal signal generator converts a digital sinusoidal signal having a target frequency into an analog sinusoidal signal. The synchronous detector extracts a target frequency component of a bioelectrical signal generated in response to an analog sinusoidal signal based on the digital sinusoidal signal. The bioimpedance analyzer calculates the bioimpedance based on the target frequency component of the bioelectrical signal. According to the inventive concept, it is possible to improve the selectivity for extracting the target frequency component of the bioelectri- (Continued)

cal signal and to reduce the area and variations of characteristics for the implementation of the integrated circuit.

12 Claims, 6 Drawing Sheets

(51) Int. Cl.
    *A61B 5/00*     (2006.01)
    *G01N 33/483*     (2006.01)

(52) U.S. Cl.
    CPC ....... *G01N 27/028* (2013.01); *G01N 33/4833* (2013.01); *A61B 5/7225* (2013.01)

(56) References Cited

U.S. PATENT DOCUMENTS

| | | | |
|---|---|---|---|
| 8,165,652 B2 | 4/2012 | Ryu et al. | |
| 8,386,028 B2* | 2/2013 | Cha | A61B 5/0537 600/547 |
| 9,351,653 B1* | 5/2016 | Harrison | A61B 5/053 |
| 10,276,910 B1* | 4/2019 | Tsironis | H03H 7/40 |
| 2003/0128768 A1* | 7/2003 | Harres | H04L 27/38 375/261 |
| 2004/0227654 A1* | 11/2004 | Yang | H03M 1/682 341/172 |
| 2013/0016982 A1* | 1/2013 | Henzler | H04B 10/50 398/161 |
| 2014/0155708 A1* | 6/2014 | Petersen | A61B 5/7278 600/490 |
| 2017/0170908 A1* | 6/2017 | Sternklar | H04B 10/50577 |
| 2017/0238865 A1 | 8/2017 | Youm et al. | |
| 2018/0306908 A1* | 10/2018 | Meng | G01S 7/4865 |

OTHER PUBLICATIONS

Ahyoung Choi et al., "Smartphone-Based Bioelectrical Impedance Analysis Devices for Daily Obesity Management", Sensors, Sep. 2, 2015, pp. 22151-22166.

* cited by examiner

BODY COMPOSITION ANALYSIS SYSTEM

CROSS-REFERENCE TO RELATED APPLICATIONS

This U.S. non-provisional patent application claims priority under 35 U.S.C. § 119 of Korean Patent Application No. 10-2018-0014770, filed on Feb. 6, 2018, the entire contents of which are hereby incorporated by reference.

BACKGROUND

The present disclosure herein relates to the processing of biological signals, and more particularly to a body composition analysis system.

As medical technology develops, a variety of electronic devices, which sense biological signals and analyze body composition based on sensed biological signals, are in development. Particularly, the body composition analysis system using the bioelectrical impedance analysis (BIA) method is attracting attention in that it may analyze the body composition by calculating the impedance inside the body through a noninvasive method. The body composition analysis system of the BIA method applies a weak electrical signal to the human body, measures the biological signal outputted through the human body, and calculates the impedance of the human body, so that body fat mass and muscle mass within the human body may be measured.

Recently, according to various interests in health, the body composition analysis system is continuously applied to mobile devices such as mobile phones or smart phones, or wearable devices such as smart watches. A body composition analysis system applied to such a mobile device or a wearable device is required to be implemented as an integrated circuit (IC) in order to ensure miniaturization and portability.

The body composition analysis system extracts and analyzes specific frequency components of the biological signal outputted through the human body, so that the bioimpedance may be analyzed. To extract specific frequency components of a biological signal, a band pass filter may be included in the body composition analysis system. The band pass filter may require a plurality of passive elements and have varying characteristics based on various environmental factors. Therefore, when the body composition analysis system is implemented as an IC, a method that may minimize area and variation of characteristics is required.

SUMMARY

The present disclosure is to provide a body composition analysis system capable of minimizing area and variations of characteristics for implementation in an integrated circuit while improving selectivity for extracting a target frequency component of a transmission signal outputted through a human body.

A body composition analysis system according to an embodiment of the inventive concept includes a sinusoidal signal generator, a synchronous detector, and a bioimpedance analyzer. The sinusoidal signal generator converts a digital sinusoidal signal having a target frequency into an analog sinusoidal signal and outputs the analog sinusoidal signal. The synchronous detector extracts a target frequency component of a bioelectrical signal generated in response to an analog sinusoidal signal based on a digital sinusoidal signal. The bioimpedance analyzer calculates the bioimpedance based on the target frequency component of the bioelectrical signal.

The sinusoidal signal generator includes a digital signal generator that generates a digital sinusoidal signal and a digital-to-analog converter that converts the digital sinusoidal signal to an analog sinusoidal signal. The digital signal generators may output the most significant bits of a digital sinusoidal signal to a synchronous detector. The sinusoidal signal generator may include a first sinusoidal signal generator for converting a first digital sinusoidal signal having a first target frequency into a first analog sinusoidal signal and outputting the same, and a second sinusoidal signal generator for converting a second digital sinusoidal signal having a second target frequency to a second analog sinusoidal signal. The body composition analysis system may further include a signal mixer for synthesizing the first and second analog sinusoidal signals.

The synchronous detector includes a multiplier and a low-pass filter. The multiplier multiplies the reference signal generated based on the digital sinusoidal signal with the bioelectrical signal to output a mixed signal. The low-pass filter may filter components below the reference frequency of the mixed signal. In this case, the low-pass filter may extract the DC (Direct Current) component of the mixed signal. The synchronous detector may generate a reference signal based on the most significant bit of the digital sinusoidal signal from the sinusoidal signal generator. The synchronous detector may generate a square wave signal having a target frequency as a reference signal based on the most significant bit signal of the digital sinusoidal signal. The body composition analysis system may further include a phase controller that adjusts the phase of the most significant bit signal of the digital sinusoidal signal and outputs the result to a synchronous detector.

A body composition analysis system according to an embodiment of the inventive concept includes first and second sinusoidal signal generators, a signal mixer, first and second synchronous detectors, and a bioimpedance analyzer. The first sinusoidal signal generator converts a first digital sinusoidal signal having a first target frequency to a first analog sinusoidal signal, and the second sinusoidal signal generator converts a second digital sinusoidal signal having a second target frequency to a second analog sinusoidal signal. The signal mixer synthesize the first and second analog sinusoidal signals to output a transmit signal. The first synchronous detector extracts a first target frequency component of the bioelectrical signal based on a multiplication operation of the bioelectrical signal and the first reference signal, and the second synchronous detector extracts a second target frequency component of the bioelectrical signal based on the multiplication of the bioelectrical signal and the second reference signal.

The first reference signal has a first target frequency component and the second reference signal has a second target frequency component. In one example, the first reference signal may be generated based on the most significant bit signal of the first digital signal, and the second reference signal may be generated based on the most significant bit signal of the second digital signal. In one example, the first reference signal may be a first analog sinusoidal signal and the second reference signal may be a second analog sinusoidal signal. In one example, the body composition analysis system may further include a reference signal generator for generating first and second reference signals.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

In the following, embodiments of the inventive concept will be described in detail so that those skilled in the art easily carry out the inventive concept.

Figure 1:
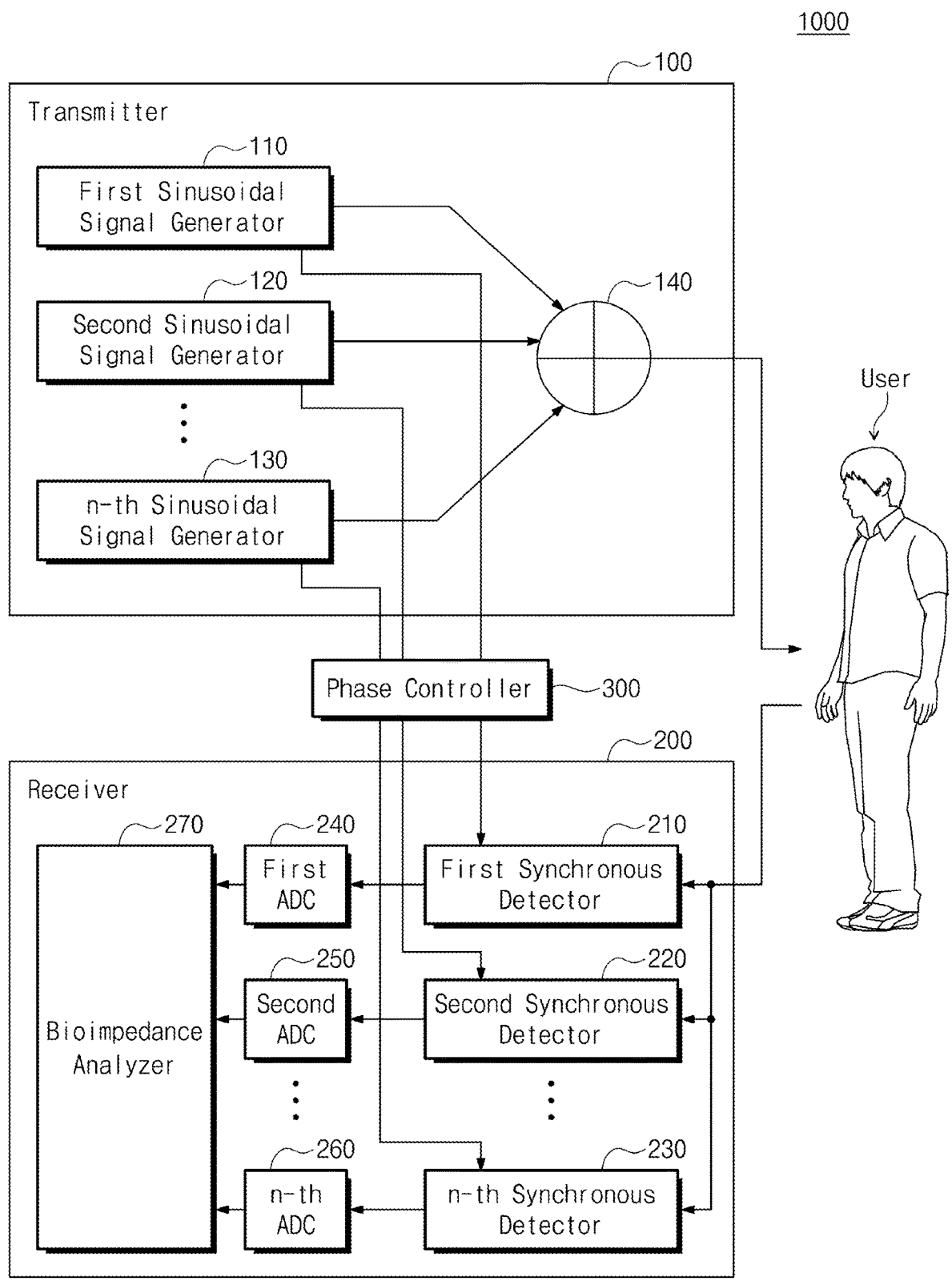
FIG. 1 is a block diagram of a body composition analysis system according to an embodiment of the inventive concept.

FIG. 1 is a block diagram of a body composition analysis system according to an embodiment of the inventive concept. Referring to FIG. 1, a body composition analysis system 1000 may include a transmitter 100, a receiver 200, and a phase controller 300. Each of the transmitter 100, the receiver 200, and the phase controller 300 may be implemented as a separate integrated circuit, or may be implemented as a single integrated circuit.

The transmitter 100 includes first to n-th sinusoidal signal generators 110 to 130 and a signal mixer 140. The transmitter 100 outputs signals having a plurality of frequencies for bioelectrical impedance analysis (BIA) using multi-frequency through the first to n-th sinusoidal signal generators 110 to 130. Through the multi-frequency BIA method, the accuracy of body composition analysis may be improved. The bioimpedance based on various body compositions of the human body may be measured and analyzed using signals having a plurality of frequencies.

Each of the first to n-th sinusoidal signal generators 110 to 130 generates first to n-th analog sinusoidal signals having different target frequencies. The number of sinusoidal signal generators is not limited. The first sinusoidal signal generator 110 may generate a first analog sinusoidal signal having a first target frequency. The second sinusoidal signal generator 120 may generate a second analog sinusoidal signal having a second target frequency different from the first target frequency. The target frequency of each of the analog sinusoidal signals may be less than a few MHz.

Each of the first to n-th sinusoidal signal generators 110 to 130 generates a digital sinusoidal signal having a target frequency and converts the generated digital sinusoidal signal into an analog sinusoidal signal. For this, each of the first to n-th sinusoidal signal generators 110 to 130 may include a digital signal generator and a digital-to-analog converter, and a detailed description thereof will be described later. Each of the first to n-th sinusoidal signal generators 110 to 130 may provide a digital sinusoidal signal or an analog sinusoidal signal to the receiver 200 through the phase controller 300, and the receiver 200 may extract a target frequency component of a signal inputted from a user USER based on signals provided from the first to n-th sinusoidal signal generators 110 to 130. Details of this will be described later.

The signal mixer 140 may synthesize the first to n-th analog sinusoidal signals. The signal mixer 140 may include an adder for synthesizing the first to n-th analog sinusoidal signals. The signal mixer 140 may add the first to n-th analog sinusoidal signals to generate a transmission signal. The transmission signal may be outputted to the user USER. For this, the body composition analysis system 1000 may further include a transmission electrode (not shown) electrically connected to the signal mixer 140 and configured to contact the user USER.

The transmitter 100 may synthesize the first to n-th analog sinusoidal signals generated at the same time to generate a transmission signal. That is, the first to n-th sinusoidal signal generators 110 to 130 may be synchronized and may output the first to n-th analog sinusoidal signals. As the first to n-th analog sinusoidal signals are synthesized and outputted to the user USER, it is possible to analyze fast bioimpedance in comparison with the case of outputting a sinusoidal signal having a different target frequency sequentially to the user USER. However, the inventive concept is not limited thereto, and each of the first to n-th sinusoidal signal generators 110 to 130 may sequentially output an analog sinusoidal signal.

The receiver 200 includes first to n-th synchronous detectors 210 to 230, first to n-th analog-to-digital converters 240 to 260, and a bioimpedance analyzer 270. The receiver 200 receives an electrical signal (hereinafter referred to as a bioelectrical signal) through which a transmission signal is outputted through the living body. The receiver 200 receives the bioelectrical signal generated in response to the transmission signal transmitted by the transmitter 100. A closed circuit may be formed between the transmitter 100 and the receiver 200 through the user USER and the receiver 200 may receive the bioelectrical signal according to the bioimpedance by the body composition of the user USER. For this, the body composition analysis system 1000 may further include a receiving electrode (not shown) electrically connected to the first to n-th synchronous detectors 210 to 230 and configured to contact a user USER.

Each of the first to n-th synchronous detectors 210 to 230 extracts the first to n-th target frequency components of the bioelectrical signal. The number of synchronous detectors is not limited, but may be equal to the number of sinusoidal signal generators. The first synchronous detector 210 may extract a first target frequency component of the bioelectrical signal. The second synchronous detector 220 may extract a second target frequency component different from the first target frequency. That is, each of the first to n-th synchronous detectors 210 to 230 may extract target frequency components corresponding to the first to n-th sinusoidal signal generators 110 to 130, respectively.

Each of the first to n-th synchronous detectors 210 to 230 extracts the first to n-th target frequency components using a synchronous detection method. Each of the first to n-th synchronous detectors 210 to 230 may multiply a reference signal having a target frequency to be extracted with a bioelectrical signal. In this case, the component having the target frequency in the bioelectrical signal may appear as a DC component in the multiplied signal. Each of the first to n-th synchronous detectors 210 to 230 may extract the DC component from the multiplied signal and output it to the first to n-th analog digital converters 240 to 260. For this, each of the first to n-th synchronous detectors 210 to 230 may include a multiplier and a low-pass filter, and a detailed description thereof will be made later.

Each of the first to n-th synchronous detectors 210 to 230 does not include a band pass filter. Generally, a band pass filter may be used to extract different target frequency components of a bioelectrical signal, and to eliminate signal distortion or noise generated when a transmission signal passes through a user USER. However, as described above, since each of the analog sinusoidal signals has a target frequency of a low frequency band lower than several MHz and analog sinusoidal signals having different target frequencies are synthesized, a high selectivity of the band pass filter is required. For this, the band pass filter may include passive components such as resistors of several hundreds of kΩ to several MΩ or greater and capacitors of about several nF to tens of nF or more. Also, since the difference between the different target frequencies is small, a complex band pass filter may be required to have a high order in order to increase the selectivity of the band pass filter. The characteristics of a passive device fabricated through an integrated circuit process may typically vary up to 20%, depending on various environmental factors such as temperature or process.

Each of the first to n-th synchronous detectors 210 to 230 has a frequency selectivity higher than that of a band pass filter, includes a small number of passive elements, and has a small area when implementing an integrated circuit. The low-pass filter included in the first to n-th synchronous detectors 210 to 230 requires a smaller number of passive elements than the band pass filter and requires a lower passive element accuracy than the band pass filter. That is, the burden on the characteristic change of the passive elements for matching the target frequency band is reduced.

Each of the first to n-th synchronous detectors 210 to 230 may receive a reference signal from the first to n-th sinusoidal signal generators 110 to 130. In order to extract a target frequency component from a bioelectrical signal, the reference signal multiplied by the bioelectrical signal may have a target frequency. Since the digital sinusoidal signal or analog sinusoidal signal generated by the first to n-th sinusoidal signal generators 110 to 130 has a target frequency, each of the first to n-th synchronous detectors 210 to 230 may receive a reference signal having a corresponding target frequency from the first to n-th sinusoidal signal generators 110 to 130. Details of this will be described later.

Each of the first to n-th analog-to-digital converters 240 to 260 converts a target frequency component of the bioelectrical signal into a digital detection signal. The number of analog to digital converters is not limited, but may be equal to the number of synchronous detectors. The first analog-to-digital converter 240 converts the first target frequency component of the bioelectrical signal into a first digital detection signal and outputs the first digital detection signal to the bioimpedance analyzer 270. The second analog-to-digital converter 250 converts the second target frequency component of the bioelectrical signal into a second digital detection signal and outputs the second digital detection signal to the bioimpedance analyzer 270.

The bioimpedance analyzer 270 may calculate and analyze the bioimpedance based on the first to n-th digital detection signals received from the first to n-th analog-to-digital converters 240 to 260. For example, the bioimpedance analyzer 270 may calculate the bioimpedance of the user USER using the magnitude of the current of the transmission signal provided to the user USER from the transmitter 100 and the magnitude of the voltage of the bioelectrical signal received by the receiver 200. In addition, the bioimpedance analyzer 270 may analyze a body composition, for example, body fat amount, muscle amount, body water amount, etc., of the user USER using a plurality of target frequency components having different frequencies.

The phase controller 300 may adjust the phase of the reference signal so that the first to n-th synchronous detectors 210 to 230 extract the target frequency component of the bioelectrical signal. When the bioelectrical signal is multiplied by the reference signal, the target frequency component of the bioelectrical signal and the phase of the reference signal are required to be the same. The phase controller 300 adjusts the phases of the signals outputted from the first to n-th sinusoidal signal generators 110 to 130 such that the phase of the target frequency component of the bioelectrical signal is the same as that of the reference signal. Each of the phase adjusted reference signal may include first to n-th reference signals having first to n-th target frequencies. Each of the first to n-th reference signals is provided to the first to n-th synchronous detectors 210 to 230.

Figure 2:
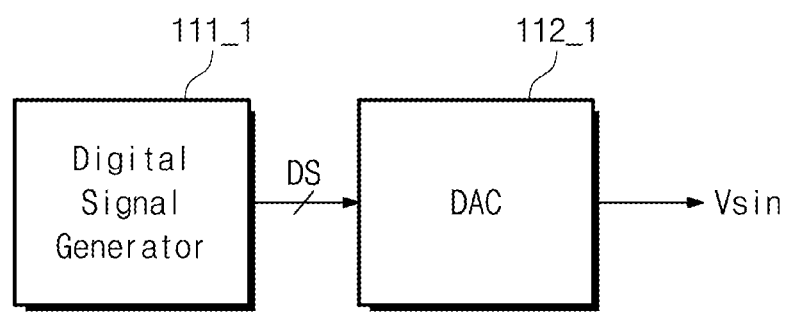
FIG. 2 is an exemplary block diagram of the sinusoidal signal generator of FIG. 1.

FIG. 2 is an exemplary block diagram of the sinusoidal signal generator of FIG. 1. The sinusoidal signal generator 110_1 of FIG. 2 may be the second sinusoidal signal generator 120 and the n-th sinusoidal signal generator 130 as well as the first sinusoidal signal generator 110 of FIG. 1. Referring to FIG. 2, the sinusoidal signal generator 110_1 may include a digital signal generator 111_1 and a digital-to-analog converter 112_1. For convenience of explanation, with reference to the reference numerals of FIG. 1, FIG. 2 will be described.

The digital signal generator 111_1 generates a digital sinusoidal signal DS. The digital signal generator 111_1 generates a sinusoidal signal having a target frequency as a digital signal. For example, when the digital signal generator 111_1 is implemented in the first sinusoidal signal generator 110, the digital signal generator 111_1 may generate a first digital sinusoidal signal having a first target frequency. For this purpose, the digital signal generator 111_1 may be implemented by Direct Digital Synthesis (DDS).

The digital signal generator 111_1 may output a digital sinusoidal signal DS having a plurality of bits to the digital-to-analog converter 112_1. For example, the digital signal generator 111_1 may output an n-bit digital sinusoidal signal DS for one time point. The n-bit digital sinusoidal signal DS may indicate the magnitude of the sinusoidal signal for a corresponding time point. In this case, the digital sinusoidal signal DS may be a digital signal quantized to $2^n$ sizes.

The digital-to-analog converter 112_1 may convert a digital sinusoidal signal DS to an analog sinusoidal signal Vsin. For example, when the digital-to-analog converter 112_1 is implemented in the first sinusoidal signal generator 110, the digital-to-analog converter 112_1 may generate a first analog sinusoidal signal having a first target frequency. The digital-to-analog converter 112_1 may determine the magnitude of the analog sinusoidal signal Vsin at the corresponding time point based on the n-bit digital sinusoidal signal DS. The digital-to-analog converter 112_1 outputs an analog sinusoidal signal Vsin to the signal mixer 140.

Since the digital sinusoidal signal DS and the analog sinusoidal signal Vsin have the target frequency, they may be used as reference signals for extracting the target frequency component of the bioelectrical signal. The reference signal may be generated based on the digital sinusoidal signal DS or the analog sinusoidal signal Vsin. In order for the reference signal to be provided to a synchronous detector that extracts a corresponding target frequency of the first to n-th synchronous detectors 210 to 230, the digital sinusoidal signal DS or the analog sinusoidal signal Vsin may be provided to the receiver 200 through the phase controller 300.

Figure 3:
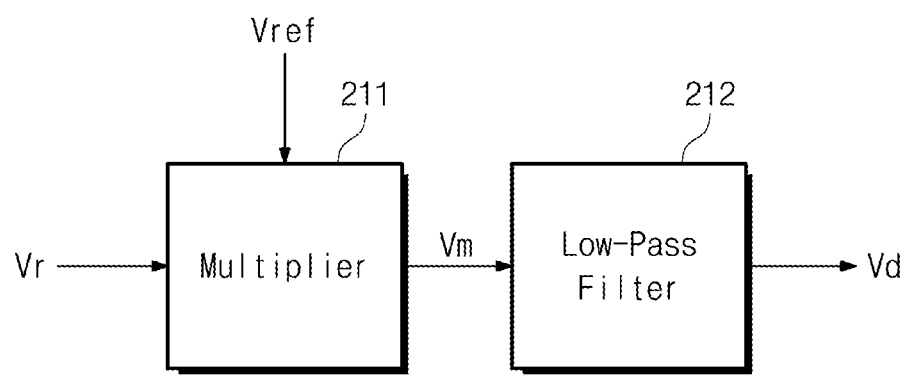
FIG. 3 is an exemplary block diagram of the synchronous detector of FIG. 1.

FIG. 3 is an exemplary block diagram of the synchronous detector of FIG. 1. The synchronous detector 210 of FIG. 3 may be the first synchronous detector 210 of FIG. 1. However, the inventive concept is not limited thereto, and the second synchronous detector 220 and the n-th synchronous detector 230 may be implemented as the synchronous detector 210 of FIG. 3. Referring to FIG. 3, the synchronous detector 210 may include a multiplier 211 and a low-pass filter 212. For convenience of description, with reference to the reference numerals of FIG. 1 or 2, FIG. 3 will be described.

The multiplier 211 multiplies the bioelectrical signal Vr by the reference signal Vref to generate a mixed signal Vm. The reference signal Vref may be a signal having a target frequency. For example, if the synchronous detector 210 is the first synchronous detector 210 of FIG. 1, the reference signal Vref may be a signal having a first target frequency. The reference signal Vref may be a sinusoidal signal or a square wave signal having a target frequency, but is not limited thereto. The reference signal Vref may be generated based on a digital sinusoidal signal DS or an analog sinusoidal signal Vsin generated from the sinusoidal signal generator 110_1, but is not limited thereto. The multiplier 211 outputs the mixed signal Vm to the low-pass filter 212.

The low-pass filter 212 may extract the DC component of the mixed signal Vm. The low-pass filter 212 may filter the components below the reference frequency in the mixed signal Vm. The DC component of the mixed signal Vm may include information on a target frequency component of the bioelectrical signal Vr according to a multiplication operation of the bioelectrical signal Vr and the reference signal Vref. That is, the target frequency component of the bioelectrical signal Vr may be extracted using the low-pass filter 212. The low-pass filter 212 removes information other than the target frequency by removing frequency components other than the reference frequency. The low-pass filter 212 may remove the distortion and noise of the signal generated when the transmission signal passes through the user USER. The low-pass filter 212 generates a detection signal Vd including a target frequency component of the bioelectrical signal Vr, and outputs the detection signal Vd to one of the first to n-th analog-to-digital converters 240 to 260.

Figure 4:
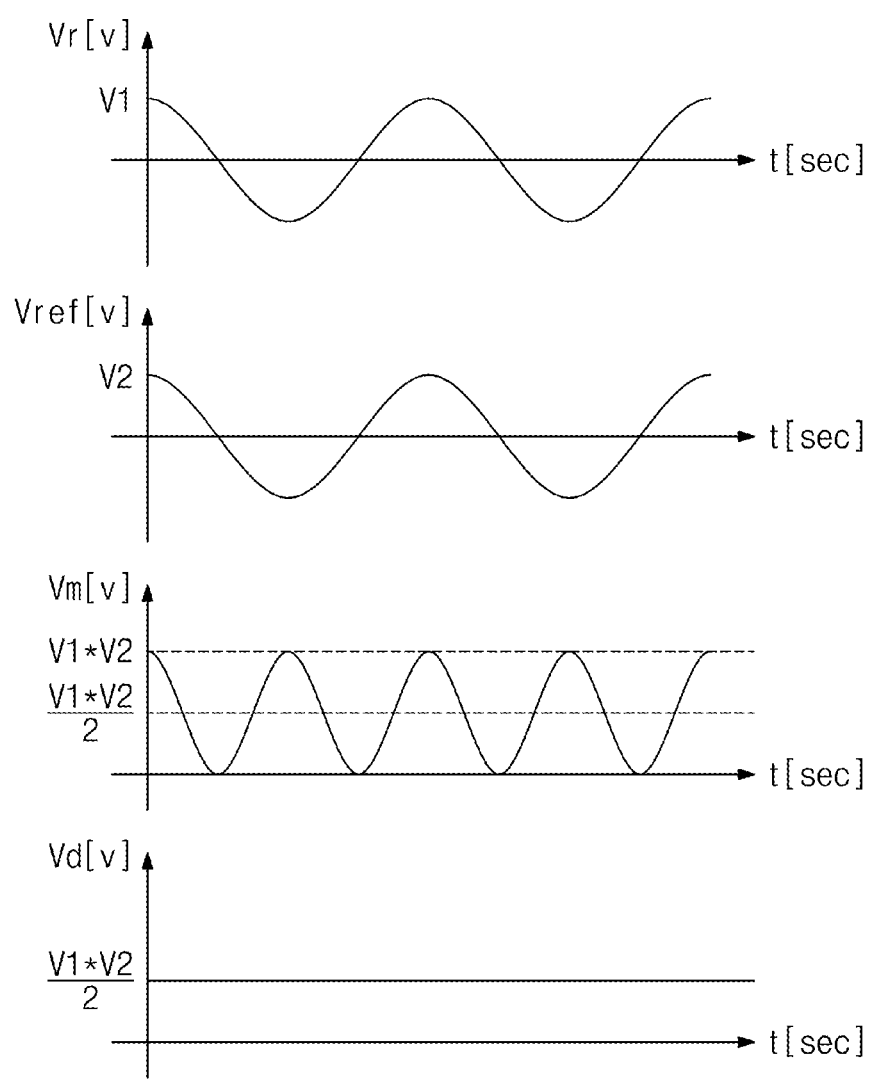
FIG. 4 is a graph showing a waveform of a bioelectrical signal, a reference signal, a mixed signal, and a detection signal over time.

FIG. 4 is a graph showing a waveform of a bioelectrical signal, a reference signal, a mixed signal, and a detection signal over time. Referring to FIG. 4, the horizontal axis is defined as time, and the vertical axis is defined as the voltage level of the bioelectrical signal Vr, the reference signal Vref, the mixed signal Vm, and the detection signal Vd. Although it is described that the vertical axis of FIG. 4 is defined as the voltage level, it is not limited thereto. For example, the vertical axis may be defined as the current level. For convenience of description, with reference to the reference numerals of FIGS. 1 to 3, FIG. 4 will be described.

Since the bioelectrical signal Vr is generated in response to a transmission signal in which a plurality of target frequencies are synthesized, the bioelectrical signal Vr may have substantially various frequency components. For convenience of explanation, the bioelectrical signal Vr shown in FIG. 4 will be understood as a bioelectrical signal Vr corresponding to a target frequency component in a bioelectrical signal having various frequency components. The bioelectrical signal Vr may be a sinusoidal signal having an amplitude of the first voltage level V1 and having a target frequency.

The reference signal Vref may be a sinusoidal signal having a target frequency. The reference signal Vref may have an amplitude of the second voltage level V2. The frequency and phase of the reference signal Vref may be the same as the target frequency component of the bioelectrical signal Vr. The reference signal Vref may be generated using a signal generated from the sinusoidal signal generator 110_1 so as to have a target frequency. For example, the reference signal Vref may be an analog sinusoidal signal Vsin outputted from the digital-to-analog converter 112_1 of FIG. 2. However, the inventive concept is not limited to this, and the reference signal Vref may be generated based on the digital sinusoidal signal DS outputted from the digital signal generator 111_1 of FIG. 2. The phase controller 300 may adjust the phase of the reference signal Vref so that the target frequency components of the reference signal Vref and the bioelectrical signal Vr have the same phase.

The mixed signal Vm may be generated by a multiplier 211 by a multiplication operation of the bioelectrical signal Vr and the reference signal Vref.

The mixed signal Vm may be equal to Equation 1.

$$Vr = V1 \cdot \cos(wt) \text{ and } Vref = V2 \cdot \cos(wt + a) \qquad \text{[Equation 1]}$$
$$Vm = \frac{1}{2} \cdot V1 \cdot V2 \cdot \cos(a) + \frac{1}{2} \cdot V1 \cdot V2 \cdot \cos(2wt + a)$$

Referring to Equation 1, the mixed signal Vm has a DC component of ½*V1*V2*cos(a) and an AC component having an amplitude of ½*V1*V2 of the target frequency and having a frequency two times the target frequency. When the phase of the target frequency component of the bioelectrical signal Vr and the phase of the reference signal Vref are the same, since a=0, the DC component of the mixed signal Vm may have a voltage level of ½*V1*V2. Since the second voltage level V2 corresponding to the amplitude of the reference signal Vref is generated and known through the body composition analysis system 1000, information on the target frequency component of the bioelectrical signal Vr may be calculated by the DC component of the mixed signal Vm.

The detection signal Vd may be a DC component of the mixed signal Vm extracted by the low-pass filter 212. The detection signal Vd may have a voltage level of ½*V1*V2. As described above, the first voltage level V1, which is amplitude for the target frequency component of the bioelectrical signal Vr, may be calculated through the detection signal Vd. The bioimpedance analyzer 270 may calculate the bioimpedance of the user USER based on the first voltage level V1. In addition, the bioimpedance analyzer 270 may further calculate voltage levels for other target frequency components to analyze the body composition of a user USER including body fat mass, muscle mass, and body water content.

Figure 5:
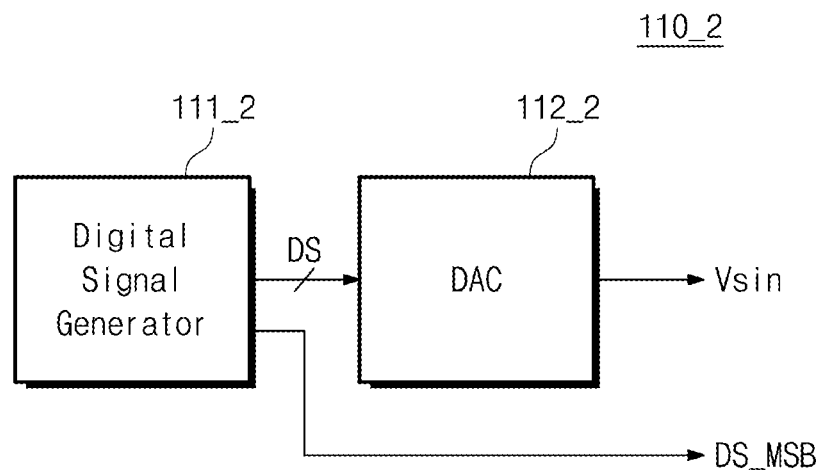
FIG. 5 is an exemplary block diagram of the sinusoidal signal generator of FIG. 1.

FIG. 5 is an exemplary block diagram of the sinusoidal signal generator of FIG. 1. The sinusoidal signal generator 110_2 of FIG. 5 may be the second sinusoidal signal generator 120 and the n-th sinusoidal signal generator 130 as well as the first sinusoidal signal generator 110 of FIG. 1. Referring to FIG. 5, the sinusoidal signal generator 110_2 may include a digital signal generator 111_2 and a digitalto-analog converter 112_2. For convenience of explanation, with reference to the reference numerals of FIG. 1, FIG. 5 will be described.

The digital signal generator 111_2 generates a digital sinusoidal signal DS, and the digital-to-analog converter 112_2 may convert a digital sinusoidal signal DS to an analog sinusoidal signal Vsin. The configuration for generating the digital sinusoidal signal DS of the digital signal generator 111_2 and the configuration for generating the analog sinusoidal signal Vsin of the digital-to-analog converter 112_2 are substantially the same as those of the digital signal generator 111_1 and digital-to-analog converter 112_1 of FIG. 2, a detailed description is omitted.

The digital signal generator 111_2 may output the most significant bit signal DS_MSB of the digital sinusoidal signal DS to the receiver 200. The most significant bit signal DS_MSB may be a signal obtained by extracting a Most Significant Bit (MSB) among a plurality of bits included in the digital sinusoidal signal DS. For example, the most significant bit signal DS_MSB may include the leftmost bit in a digital sinusoidal signal DS composed of a bit string of n bits. The most significant bit may indicate the polarity of the digital sinusoidal signal DS. For example, when the sinusoidal signal is positive, the most significant bit may have a value of 1, and when the sinusoidal signal is negative, the most significant bit may have a value of 0.

The most significant bit signal DS_MSB may be used to generate a reference signal provided to each of the first to n-th synchronous detectors 210 to 230. The most significant bit signal DS_MSB may be used to generate a reference signal having a square wave. The most significant bit signal DS_MSB has a target frequency and may represent a waveform in which 1 and 0 are repeated. Thus, the receiver 200 outputs a DC voltage greater than zero when the most significant bit signal DS_MSB has a value of 1, and outputs a DC voltage smaller than 0 when the most significant bit signal DS_MSB has a value of 0, thereby generating a reference signal having a square wave.

Although it is shown that the digital signal generator 111_2 outputs the digital sinusoidal signal DS and the MSB signal DS_MSB using separate output terminals, the inventive concept is not limited thereto. The digital signal generator 111_2 outputs a digital sinusoidal signal DS from an output terminal of the digital sinusoidal signal DS to a synchronous detector included in the receiver 200, and selectively outputs the digital sinusoidal signal DS corresponding to the most significant bit to the receiver 200. For example, a switch for selective output of the most significant bits may be provided.

Figure 6:
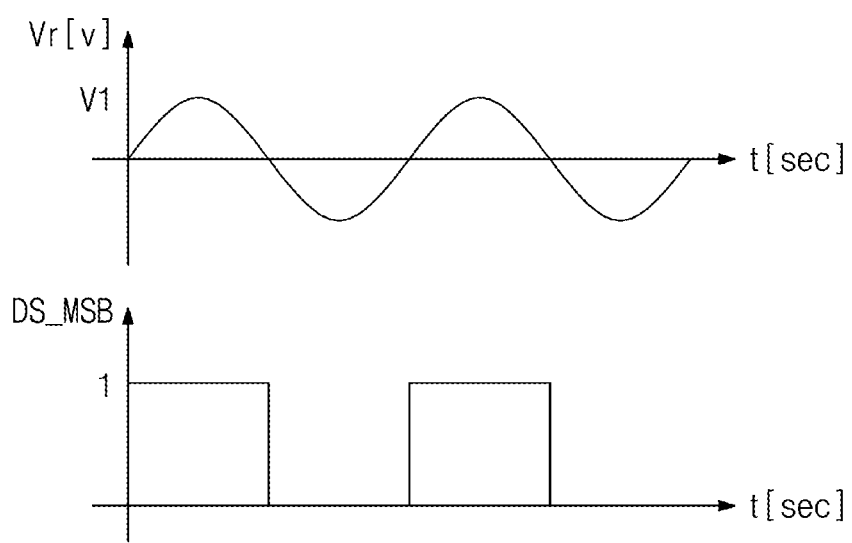
FIG. 6 is a graph showing waveforms of an analog sinusoidal signal and a most significant bit signal over time.

FIG. 6 is a graph showing waveforms of an analog sinusoidal signal and a most significant bit signal over time. Referring to FIG. 6, the horizontal axis is defined as time, and the vertical axis is defined as the magnitude of an analog sinusoidal signal (Vsin) and a most significant bit signal DS_MSB of a digital sinusoidal signal. For convenience of explanation, with reference to the reference numerals of FIG. 5, FIG. 6 will be described.

An analog sinusoidal signal Vsin has an amplitude of the transmission voltage level V1 and may be a sinusoidal signal having a target frequency. An analog sinusoidal signal Vsin may be generated based on a digital sinusoidal signal DS generated from the digital signal generator 111_2. A digital sinusoidal signal DS may have a binary value of n bits for one time point. For example, a digital sinusoidal signal DS may have a binary value of 4 bits, and when the digital sinusoidal signal DS has a value of '1000', the analog sinusoidal signal Vsin may have a voltage level of 0. When the digital sinusoidal signal DS has a value of '1111', the analog sinusoidal signal Vsin may have a voltage level of V1. When the digital sinusoidal signal DS has a value of '0000', the analog sinusoidal signal may have a voltage level of −V1.

The most significant bit signal DS_MSB is generated based on the most significant bit value in the n-bit digital sinusoidal signal DS. When the analog sinusoidal signal Vsin is positive, the most significant bit of the digital sinusoidal signal DS has a value of 1. For example, when a digital sinusoidal signal DS has a binary value of 4 bits, at a time point where the analog sinusoidal signal Vsin has a voltage level of 0 or more, the digital sinusoidal signal DS may have a value of '1000' to '1111'. In this case, the most significant bit signal DS_MSB has a high level. When the analog sinusoidal signal Vsin is negative, the most significant bit of the digital sinusoidal signal DS has a value of 0. For example, when a digital sinusoidal signal DS has a binary value of 4 bits, at a time point where the analog sinusoidal signal Vsin has a voltage level below 0, the digital sinusoidal signal DS may have a value of '0000' to '0111'. In this case, the most significant bit signal DS_MSB has a low level.

The most significant bit signal DS_MSB may have a waveform in which the high level and the low level are repeated according to the target frequency. The most significant bit signal DS_MSB is a square wave signal. Accordingly, the most significant bit signal DS_MSB may be used to generate a reference signal having a square wave. In this case, a separate configuration for generating a reference signal having a target frequency may not be required, and the area of the body composition analysis system 1000 may be reduced.

Figure 7:
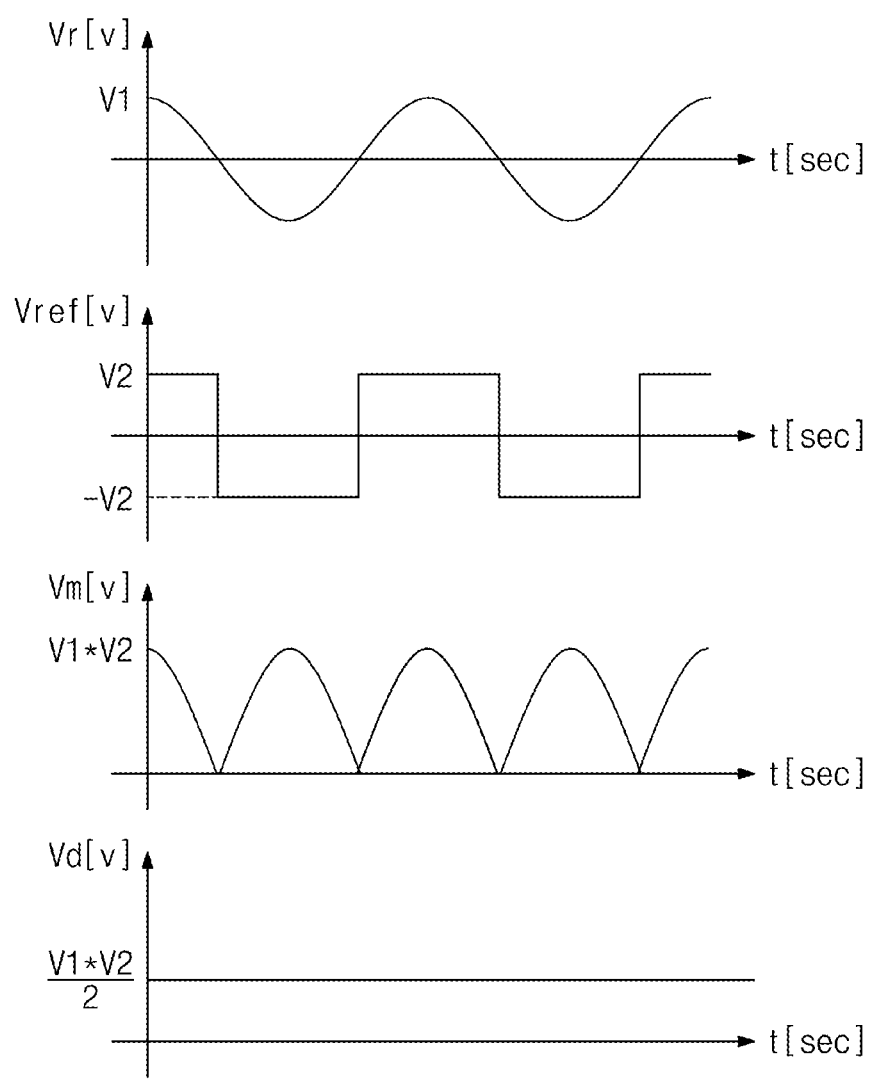
FIG. 7 is a graph showing a waveform of another bioelectrical signal, reference signal, mixed signal, and detection signal over time.

FIG. 7 is a graph showing a waveform of another bioelectrical signal, reference signal, mixed signal, and detection signal over time. Referring to FIG. 7, the horizontal axis is defined as time, and the vertical axis is defined as the voltage level of the bioelectrical signal Vr, the reference signal Vref, the mixed signal Vm, and the detection signal Vd. Although it is described that the vertical axis of FIG. 7 is defined as the voltage level, it is not limited thereto. For example, the vertical axis may be defined as the current level. The bioelectrical signal Vr will be understood as a bioelectrical signal Vr corresponding to a target frequency component in a bioelectrical signal having various frequency components such as the bioelectrical signal Vr in FIG. 4. The bioelectrical signal Vr has a target frequency and may have an amplitude of the first voltage level V1. For convenience of description, with reference to the reference numerals of FIGS. 1, 3, and 5, FIG. 7 will be described.

The reference signal Vref may be a square wave signal having a target frequency. The reference signal Vref may have an amplitude of the second voltage level V2. The reference signal Vref may be repeated between the voltage level V2 and the voltage level −V2. The frequency and phase of the square wave signal may be the same as the target frequency component of the bioelectrical signal Vr. The reference signal Vref may be generated based on the most significant bit signal DS_MSB outputted from the digital signal generator 111_2 so as to have the target frequency. The phase controller 300 may adjust the phase of the reference signal Vref so that the target frequency components of the reference signal Vref and the bioelectrical signal Vr have the same phase.

The mixed signal Vm may be generated by a multiplier 211 by a multiplication operation of the bioelectrical signal Vr and the reference signal Vref. The mixed signal Vm may be equal to Equation 2.

$$Vm = \frac{1}{2} \cdot V1 \cdot V2 + \frac{1}{2} \cdot V1 \cdot$$
$$V2 \cdot (a1 \cdot \cos(wt) + a2 \cdot \cos(2wt) + a3 \cdot \cos(3wt) + \ldots)$$ [Equation 2]

Referring to Equation 2, since the square wave signal includes a plurality of harmonic components, the mixed signal Vm includes a DC component and an AC component having a plurality of frequencies. However, as shown in FIG. 4, the DC component of the mixed signal Vm has a voltage level of ½*V1*V2. Since the second voltage level V2 corresponding to the amplitude of the reference signal Vref is known, information on the target frequency component of the bioelectrical signal Vr may be calculated by the DC component of the mixed signal Vm.

The detection signal Vd may be a DC component of the mixed signal Vm extracted by the low-pass filter 212. The detection signal Vd may have a voltage level of ½*V1*V2. Through this, the first voltage level V1 may be calculated, and the bioimpedance analyzer 270 may calculate the bioimpedance of the user USER based on the first voltage level V1. In addition, the bioimpedance analyzer 270 may further calculate voltage levels for other target frequency components to analyze the body composition of a user USER including body fat mass, muscle mass, and body water content.

Figure 8:
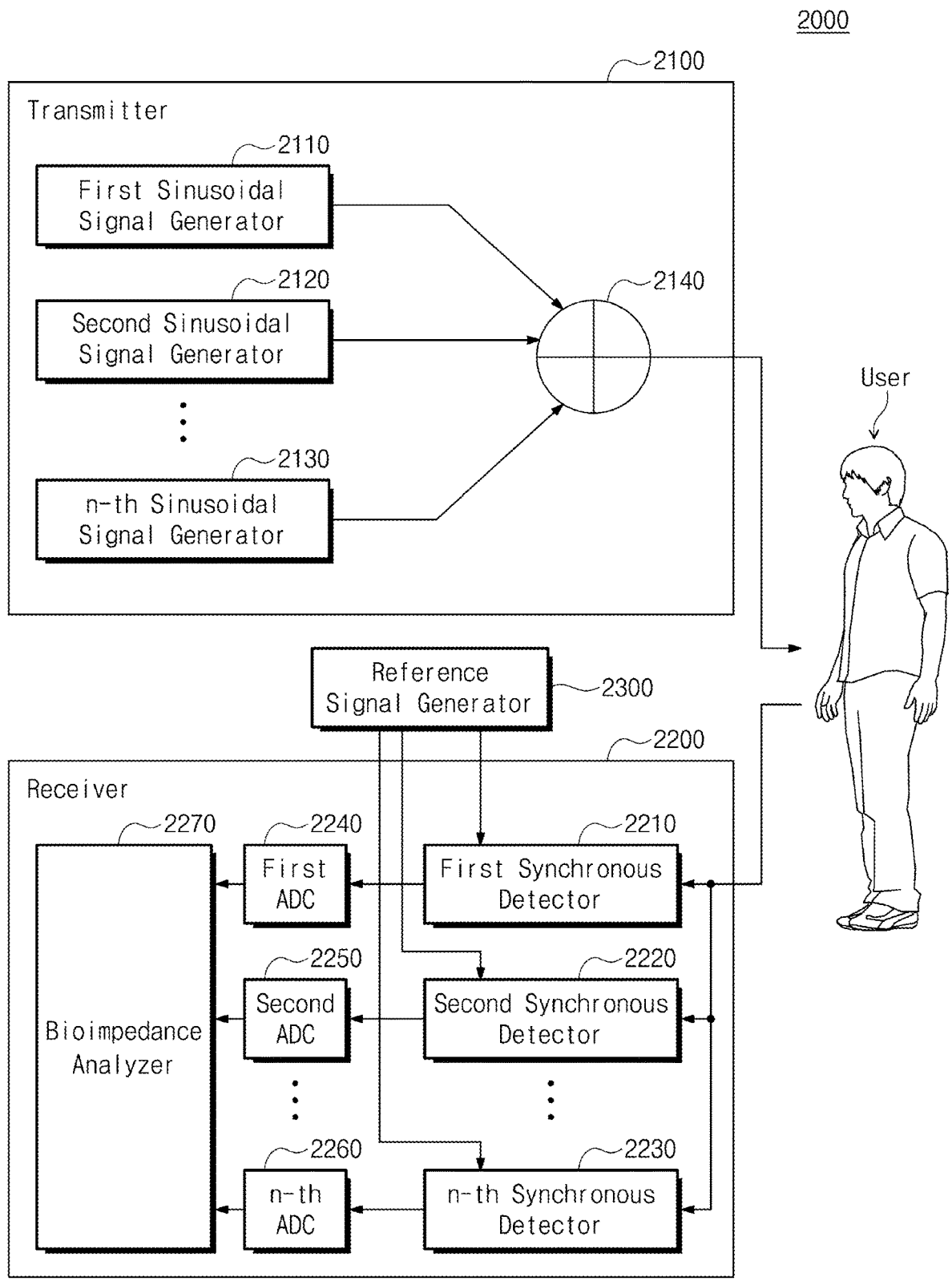
FIG. 8 is a block diagram of a body composition analysis system according to an embodiment of the inventive concept.

FIG. 8 is a block diagram of a body composition analysis system according to an embodiment of the inventive concept. Referring to FIG. 8, a body composition analysis system 2000 includes a transmitter 2100, a receiver 2200, and a reference signal generator 2300. The transmitter 2100 includes first to n-th sinusoidal signal generators 2110 to 2130 and a signal mixer 2140. The receiver 2200 includes first to n-th synchronous detectors 2210 to 2230, first to n-th analog-to-digital converters 2240 to 2260, and a bioimpedance analyzer 2270. The configurations included in the transmitter 2100 and the receiver 2200 are substantially the same as those of the transmitter 100 and the receiver 200 in FIG. 1, so that detailed description is omitted.

The reference signal generator 2300 may generate first to n-th reference signals having different target frequencies. The reference signal generator 2300 generates a first reference signal having a first target frequency and outputs the first reference signal to the first synchronous detector 2210, and generates a second reference signal having a second target frequency and outputs the second reference signal to the second synchronous detector 2220. Here, the first target frequency is equal to the frequency of the first analog sinusoidal signal generated from the first sinusoidal signal generator 2110, and the second target frequency is equal to the frequency of the second analog sinusoidal signal generated from the second sinusoidal signal generator 2120.

The first to n-th reference signals may be sinusoidal or square wave signals, but are not limited thereto. The reference signal generator 2300 may generate first to n-th reference signals having waveforms such as the reference signal Vref of FIG. 4 or the reference signal Vref of FIG. 7. The reference signal generator 2300 generates a reference signal having the same phase as the target frequency component of the bioelectrical signal supplied from the user USER to the receiver 2200. That is, the reference signal generator 2300 may perform the function of the phase controller 300 of FIG. 1 to adjust the phase of the first to n-th reference signals.

The body composition analysis system according to the embodiment of the inventive concept may minimize the area and the variations of the characteristics for the implementation of the integrated circuit while improving the selectivity for extracting the target frequency component using the synchronous detector. In addition, the body composition analysis system according to the embodiment of the inventive concept generates a reference signal using a sinusoidal signal generator for providing an electrical signal to the human body, thereby minimizing hardware for implementing a synchronous detector.

Although the exemplary embodiments of the inventive concept have been described, it is understood that the inventive concept should not be limited to these exemplary embodiments but various changes and modifications may be made by one ordinary skilled in the art within the spirit and scope of the inventive concept as hereinafter claimed.

What is claimed is:

1. A body composition analysis system comprising:
  a transmitter configured to transmit a transmission signal to a body of a user;
  a receiver configured to receive a bioelectrical signal from the body of the user and calculate a bioimpedance using the bioelectrical signal; and
  a phase controller configured to receive a plurality of sinusoidal signals from the transmitter, and to generate a plurality of reference signals by adjusting a phase of a frequency of each of the plurality of sinusoidal signals, the plurality of reference signals respectively corresponding to the plurality of sinusoidal signals,
  wherein the transmitter comprises:
  a plurality of sinusoidal signal generators configured to respectively generate the plurality of sinusoidal signals having different target frequencies; and
  a signal mixer configured to synthesize the plurality of sinusoidal signals and generate the transmission signal,
  wherein the receiver comprises:
  a plurality of synchronous detectors respectively corresponding to the plurality of sinusoidal signal generators, each of the plurality of synchronous detectors configured to extract a corresponding one of a plurality of target frequency components from the bioelectrical signal using a corresponding one of the plurality of reference signals;
  a plurality of analog-to-digital converters, each of which is configured to convert a corresponding one of the plurality of target frequency components into a corresponding one of a plurality of digital detection signals; and
  a bioimpedance analyzer configured to calculate a bioimpedance using the plurality of digital detection signals,
  wherein each of the plurality of synchronous detectors comprises:
  a multiplier configured to multiply the bioelectrical signal and a corresponding one of the reference signals to output a multiplied signal; and
  a low-pass filter configured to receive the multiplied signal from the multiplier and filter frequency components of the multiplied signal that are below a reference frequency of the multiplied signal, and
  wherein the phase controller is further configured to adjust the phase of the frequency of each of the plurality of sinusoidal signals so that a phase of a frequency of each of the plurality of reference signals is equal to a phase of a corresponding one of the target frequency components of the bioelectrical signal.

2. The system of claim 1, wherein each of the plurality of sinusoidal signal generators comprises:
   a digital signal generator configured to generate a digital sinusoidal signal; and
   a digital-to-analog converter configured to convert the digital sinusoidal signal into an analog sinusoidal signal,
   wherein the signal mixer synthesizes a plurality of analog sinusoidal signals generated by the plurality of sinusoidal signal generators to generate the transmission signal.

3. The system of claim 2, wherein each of the plurality of synchronous detectors receives a most significant bit signal of a digital sinusoidal signal from a corresponding sinusoidal signal generator and generates a reference signal using a value of the most significant bit signal of the digital sinusoidal signal.

4. The system of claim 3, wherein said each of the plurality of synchronous detectors generates the reference signal that is a square wave signal having a target frequency according to the value of the most significant bit signal of the digital sinusoidal signal.

5. The system of claim 1, wherein the low-pass filter extracts a DC (Digital Current) component from the multiplied signal.

6. The system of claim 1, wherein the plurality of sinusoidal signal generators comprises:
   a first sinusoidal signal generator configured to convert a first digital sinusoidal signal having a first target frequency into a first analog sinusoidal signal and output the first analog sinusoidal signal; and
   a second sinusoidal signal generator configured to convert a second digital sinusoidal signal having a second target frequency different from the first target frequency to a second analog sinusoidal signal and output the second analog sinusoidal signal,
   wherein the plurality of synchronous detectors comprises:
   a first synchronous detector configured to extract a first target frequency component from the bioelectrical signal using a first reference signal corresponding to the first digital sinusoidal signal; and
   a second synchronous detector configured to extract a second target frequency component from the bioelectrical signal using a second reference signal corresponding to the second digital sinusoidal signal.

7. The system of claim 6, wherein the signal mixer synthesizes the first analog sinusoidal signal and the second analog sinusoidal signal to generate the transmission signal.

8. The system of claim 1,
   wherein the phase controller is configured to adjust a phase of a most significant bit signal of a digital sinusoidal signal generated by each of the plurality of sinusoidal signal generators and output a phase-adjusted signal to a corresponding one of the plurality of synchronous detectors as a corresponding reference signal.

9. A body composition analysis system comprising:
   a transmitter configured to transmit a transmission signal to a body of a user; and
   a receiver configured to receive a bioelectrical signal from the body of the user and configured to calculate a bioimpedance using the bioelectrical signal,
   wherein the transmitter comprises:
   a first sinusoidal signal generator configured to generate a first digital sinusoidal signal having a first target frequency and convert the first digital sinusoidal signal into a first analog sinusoidal signal;
   a second sinusoidal signal generator configured to generate a second digital sinusoidal signal having a second target frequency different from the first target frequency and convert the second digital sinusoidal signal into a second analog sinusoidal signal; and
   a signal mixer configured to synthesize the first and the second analog sinusoidal signals and output the transmission signal, and
   wherein the receiver comprises:
   a first synchronous detector configured to extract a first target frequency component of the bioelectrical signal by performing a multiplication operation of the bioelectrical signal and a first reference signal;
   a second synchronous detector configured to extract a second target frequency component of the bioelectrical signal by performing a multiplication operation of the bioelectrical signal and a second reference signal; and
   a bioimpedance analyzer configured to calculate the bioimpedance using the extracted first and second target frequency components,
   wherein the first synchronous detector comprises:
   a first multiplier configured to multiply the first reference signal and the bioelectrical signal to generate a first multiplied signal; and
   a first low-pass filter configured to filter frequency components below a reference frequency of the first multiplied signal, and
   wherein the second synchronous detector comprises:
   a second multiplier configured to multiply the second reference signal and the bioelectrical signal to generate a second multiplied signal; and
   a second low-pass filter configured to filter frequency components below a reference frequency of the second multiplied signal.

10. The system of claim 9, wherein the first reference signal is generated using a most significant bit signal of the first digital sinusoidal signal and the second reference signal is generated using a most significant bit signal of the second sinusoidal digital signal.

11. The system of claim 9, wherein the first reference signal is the first analog sinusoidal signal and the second reference signal is the second analog sinusoidal signal.

12. The system of claim 9, further comprising a reference signal generator configured to generate the first reference signal having the first target frequency and output the first reference signal to the first synchronous detector, and generate the second reference signal having the second target frequency and output the second reference signal to the second synchronous detector.

* * * * *